United States Patent
Breach et al.

(10) Patent No.: US 6,825,460 B2
(45) Date of Patent: Nov. 30, 2004

(54) ION MOBILITY SPECTROMETERS

(75) Inventors: James Andrew Breach, Watford (GB); Robert Brian Turner, Chesham (GB)

(73) Assignee: Smith Detection-Watford, London (GB)

( * ) Notice: Subject to any disclaimer, the term of this patent is extended or adjusted under 35 U.S.C. 154(b) by 460 days.

(21) Appl. No.: 10/025,006

(22) Filed: Dec. 19, 2001

(65) Prior Publication Data

US 2002/0088936 A1 Jul. 11, 2002

Related U.S. Application Data

(63) Continuation of application No. PCT/GB00/02390, filed on Jun. 21, 2000.

(30) Foreign Application Priority Data

Jun. 23, 1999 (GB) .............................. 9914552

(51) Int. Cl.[7] .............................................. H01J 49/04
(52) U.S. Cl. ...................... 250/287; 250/288; 250/292
(58) Field of Search ................................ 250/287, 282, 250/288, 292

(56) References Cited

U.S. PATENT DOCUMENTS 5,554,846 A * 9/1996 Regiec et al. ............... 250/288
5,587,581 A * 12/1996 Stroosnyder ................ 250/287

* cited by examiner

*Primary Examiner*—John R. Lee
*Assistant Examiner*—James J. Leybourne
(74) *Attorney, Agent, or Firm*—Wallenstein Wagner & Rockey, Ltd.

(57) ABSTRACT

An ion mobility spectrometer system comprising: an ion mobility detector; a gas/vapor circulating system for the ion mobility detector into which samples of gases and vapors of interest may be drawn for detection by the ion mobility spectrometer; the circulating system comprising an ion mobility cell, means for drying and/or cleaning the circulating gases/vapors in the circulating system, a dopant source, and means for causing circulation of the gases/vapors within the circulating system; in which the dopant source and the means for drying and/or cleaning the circulating gases/vapors are combined, whereby the need for a physically separate dopant source for the system is obviated. The dopant source material may be combined with the material for drying and or cleaning the circulating gases/vapors.

15 Claims, 1 Drawing Sheet

ION MOBILITY SPECTROMETERS

This Application is a continuation of International Application No. PCT/GB00/02390, with an international filing date of 21 Jun. 2000, now pending (which is hereby incorporated by reference).

DESCRIPTION

1. Technical Field

The present invention relates to ion mobility spectrometers used for gas and vapour detection, and more particularly to ion mobility spectrometer systems in which the system is "doped", or has added to it, a low concentration of a trace reagent vapour or vapours (the "dopant") e.g. to improve the sensitivity of the system to gases or vapours of interest, or to improve the rejection of interfacing materials (i.e. those which may otherwise give rise to a response interfering with detection of gases and vapours of interest).

2. Background of the Invention

The use of dopants in Ion Mobility Spectrometer (IMS) systems is well known and the principles involved have been described in the literature, for example, in the introduction to EP-A-219602.

Dopant sources commonly consist of a sealed container with a permeation capability containing the chosen dopant material, with the container incorporated in the circulating system of the IMS detector, comprising the ion mobility cell, means such as a sieve pack for drying and cleaning the recirculating gases in the system, the dopant source, and a pump, into which samples of gases or vapours of interest, usually air-borne, are drawn for analysis.

SUMMARY OF THE INVENTION

In accordance with one aspect, the present invention consists in an ion mobility spectrometer system in which the dopant material is physically combined with molecular sieve material, whereby the need for a physically separate dopant source for the system is obviated.

In accordance with another aspect, the invention consists in a combined dopant source and molecular sieve, for use, for example, with an ion mobility spectrometer.

In accordance with a still further aspect the invention consists in a method of physically or chemically combining a molecular sieve material with a dopant material to provide a combined dopant and molecular sieve for use with an ion mobility spectrometer.

The invention provides a number of advantages over current practice in which separate dopant sources and molecular sieve packs are employed.

For example, in hand-held or body-worn IMS equipment, space within the equipment housing is at a premium, and use of a combined dopant source/molecular sieve reduces the space requirement of the circulating system.

Additionally, and especially in small instruments, there is a need to regularly change the molecular sieve. By providing a combined sieve and dopant source in a single pack, a dopant change, desirable for maintaining a consistent level of dopant within the circulating system, is provided at the same time by a single action.

Current practice requires dopant sources associated with IMS circulating systems to be heated when the instrument is operated at low temperatures. With a combined sieve and dopant source it has unexpectedly been found possible to maintain dopant levels within the circulating system at low temperatures without the need for heating, thereby further simplifying and reducing the space and power requirements of the instrument.

It has been found that combination of the dopant and the sieve material provides the required level of sensitisation of the IMS instrument to samples of interest and/or rejection of interferents.

Use of the combined dopant and sieve material within the circulating system of an IMS instrument, has also been found to improve dopant capability over a range of ambient temperatures from −30 C. to +50 C., even without heating.

Although it might be expected that applying dopant to a sieve would increase water takeup, and hence reduce the useful life of the product, the applicants have found in practice that that is not in fact the case.

In operation ambient air, which may contain gas or vapour of interest, is drawn into the circulatory system, by way of an inlet system, not here shown, and passed through the IMS cell 12 which is able, in association with conventional electronic instrumentation not here shown, to provide an electrical output representative of the presence and/or the quantity of a gas or vapour of interest in the ambient air sampled.

Figure 1:
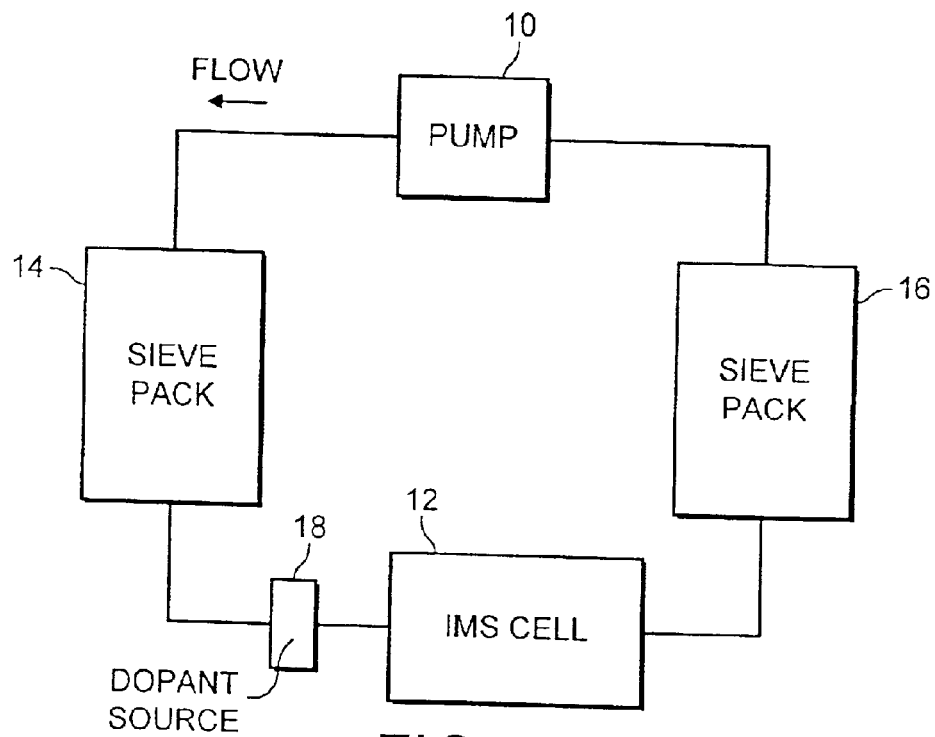
FIG. 1 of the accompanying drawings shows a simplified block diagram of a conventional ion mobility spectrometer employing a closed-loop recirculatory system, comprising a pump 10, an IMS cell 12, a pair of molecular sieve packs 14,16 for drying the carrier gas, most usually air, in the recirculatory system, and a dopant source 18, for providing the required level of dopant for sensitivity enhancement, and/or interferent rejection.
Figure 2:
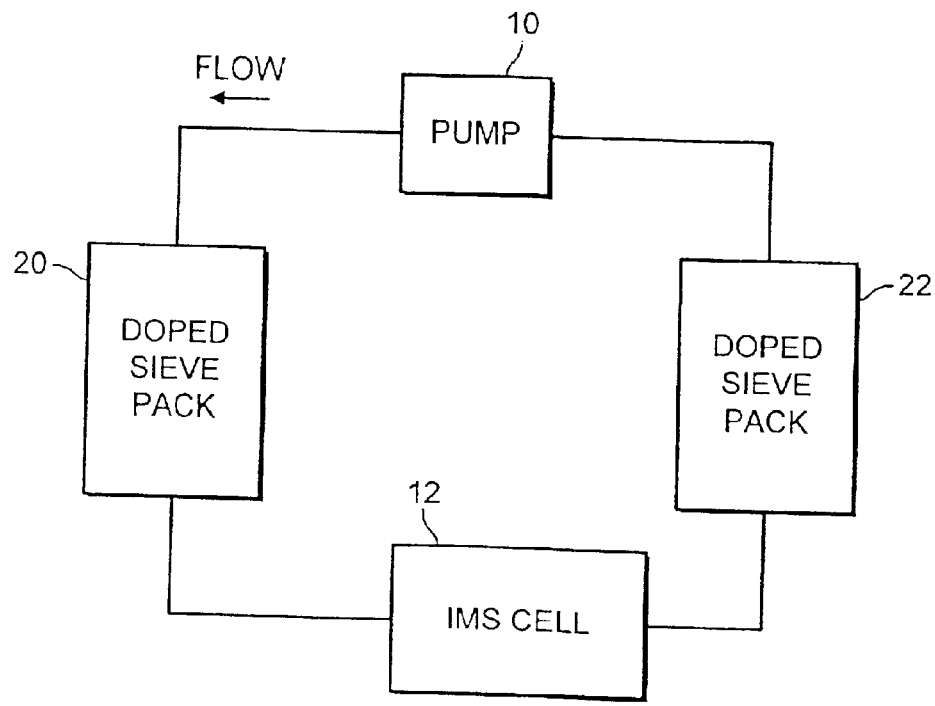

FIG. 2 shows the same instrument as is shown in FIG. 1, only with the original pair of molecular sieve packs and the dopant source replaced with a pair of combined dopant molecular sieve packs 20, 22. The sieve may be of any standard material, such as an alumino silicate (Zeolite).

DETAILED DESCRIPTION OF THE PREFERRED EMBODIMENTS

The required combination of mixed sieve and dopant material may be produced by placing the dried molecular sieve material in a sealed vessel with the correct mass of doping material, and agitating and preferably heating the mixture to 50 C. for some twelve hours.

The combination of the materials may be achieved at higher or lower temperatures, given an appropriate modification of the time to permit combination. The mixture does not always have to be heated, although to get good distribution of the dopant it is preferably for it to be agitated.

The combined material may also be made by passing a dry inert gas stream containing the dopant material at a fixed level over the molecular sieve material and allowing the molecular sieve material to absorb the dopant material.

The mechanism by which dopant material is adsorbed on to the molecular sieve is a reversible physical adsorption, meaning that with a given mass of material adsorbed on to the sieve at a given temperature the partial pressure of the adsorbed dopant material over the sieve is constant.

In an IMS system where there is carrier gas flow over the combined dopant/sieve material, and leakage of the carrier from the system, the adsorbed dopant material will be removed from the sieve material.

In a closed recirculating system, adsorbed material will be released into the carrier gas, but subsequently replaced in the sieve material, thereby maintaining a continuing constant level of dopant within the system.

By way of example, a combination of ammonium carbamate dopant, and a 13X (10A) pore size molecular sieve material, combined in the proportion of between 0.1% to 5% by weight of dopant to sieve material, was used with an ion mobility spectrometer such as shown in FIG. 2 of the drawings. Other concentrations may be used, depending upon the dopant, for example up to about 10%. The most preferred range is normally about 2 to 5%. Other pore sizes could also be used, for example 3A, 4A or 5A.

The spectral response of the three target compounds chosen for study: DMMP (0,0-Dimethyl Methane Phosphonate); TEP (Triethyl Phosphate); and DPM (Dipropylene Glycol Mono Methyl Ether); using the specified combined dopant/molecular sieve material, remained sensibly constant over a temperature range of −30 C. to +50 C.

It will be apparent that other doping compounds may be employed, chosen to provide a dopant level in a required range. In one embodiment, the dopant is preferably ammonia, or ammonia with $CO_2$.

Other absorbent materials may also be employed in the manufacture of combined dopant/sieve materials.

It has been found that the system described is longer lasting than a comparable standard permeation source and sieve system, and has a greater shelf-life.

Although the described example employs a combined dopant/sieve as the only dopant source within the system, the combined dopant/sieve may be used in an instrument system in addition to a standard dopant source, in order to provide multiple doping of the system, or to provide additional doping, for instance to support the standard permeation dopant source at low temperatures. For example, one may wish to use a very heavy molecular mass dopant in association with a very light one. The only way to achieve that, otherwise, would be by providing a very large and heavy dopant source.

What is claimed is:

1. An ion mobility spectrometer system comprising:

an ion mobility detector;

a gas/vapour circulating system for the ion mobility detector into which samples of gases and vapours of interest may be drawn for detection;

the circulating system comprising an ion mobility cell, means for drying and/or cleaning the circulating gases/vapours in the circulating system, a dopant source, and means for causing circulation of the gases/vapours within the circulating system;

in which the dopant source and the means for drying and/or cleaning the circulating gases/vapours are combined, whereby the need for a physically separate dopant source for the system is obviated.

2. An ion mobility spectrometer in accordance with claim 1 in which the dopant source material is physically combined with the material for drying and or cleaning the circulating gases/vapours.

3. An ion mobility spectrometer in accordance with claim 2 in which the material for drying and/or cleaning the circulating gases/vapours is a molecular sieve material.

4. An ion mobility spectrometer in accordance with claim 1 in which at least one further dopant source is used in addition to the combined dopant source and means for drying and cleaning of the circulating gases/vapours.

5. An ion mobility spectrometer system in accordance with claim 1 in which the dopant material is ammonium carbamate, and the molecular sieve material is 13X pore size material.

6. An ion mobility spectrometer system in accordance with claim 5 in which the dopant material and the molecular sieve material are combined in the proportions of between 0.1% to 0.5% by weight of dopant material to molecular sieve material.

7. An ion mobility spectrometer system in accordance with claim 5 in which the combined dopant and molecular sieve material is produced by heating the dopant material and the molecular sieve material together in a sealed vessel.

8. An ion mobility spectrometer in accordance with claim 5 in which the combined dopant and molecular sieve material is produced by passing a dry inert gas stream containing the dopant material at a fixed level over the molecular sieve material, whereby the molecular sieve material absorbs the dopant material.

9. An ion mobility spectrometer in accordance with claim 1 in which the combined dopant and molecular sieve material is produced by agitating together the dopant material and the molecular sieve material.

10. An ion mobility spectrometer in accordance with claim 1 in which the molecular sieve material has a pore size of 13X, 3A, 4A or 5A.

11. An ion mobility spectrometer in accordance with claim 1 in which the dopant material is ammonia or ammonia in $CO_2$.

12. An ion mobility spectrometer in accordance with claim 1 in which the dopant material and the molecular sieve material are combined in the proportions of between 2 and 5% by weight of dopant material to molecular sieve material.

13. An ion mobility spectrometer in accordance with claim 1 in which the dopant material and the molecular sieve material are combined in the proportions of between 0.1 and 10% by weight of dopant material to molecular sieve material.

14. An ion mobility spectrometer system in accordance with claim 6 in which the combined dopant and molecular sieve material is produced by heating the dopant material and the molecular sieve material together in a sealed vessel.

15. An ion mobility spectrometer in accordance with claim 6 in which the combined dopant and molecular sieve material is produced by passing a dry inert gas stream containing the dopant material at a fixed level over the molecular sieve material, whereby the molecular sieve material absorbs the dopant material.

* * * * *